United States Patent

Matsunaga

[11] Patent Number: 5,998,391
[45] Date of Patent: Dec. 7, 1999

[54] MICROBICIDAL COMPOSITION

[75] Inventor: Rei Matsunaga, Kobe, Japan

[73] Assignee: Sumitomo Chemical Company, Limited, Osaka-fu, Japan

[21] Appl. No.: 09/093,409

[22] Filed: Jun. 9, 1998

Related U.S. Application Data

[62] Division of application No. 08/808,552, Feb. 28, 1997, Pat. No. 5,798,384.

[30] Foreign Application Priority Data

Feb. 29, 1996 [JP] Japan ................................ 8-043705

[51] Int. Cl.$^6$ ............................ A01N 37/52; A01N 57/18
[52] U.S. Cl. ............................................ 514/141; 514/508
[58] Field of Search ...................... 514/508, 141

[56] References Cited

U.S. PATENT DOCUMENTS 5,563,159 10/1996 Kusaba et al. .................... 514/346

FOREIGN PATENT DOCUMENTS 10656351 6/1995 European Pat. Off. .

OTHER PUBLICATIONS

Tom Lin, The Pesticide Manual Incorporating The Agrochemicals Handbook, 10th Ed (1995) pp. 530–532.
Tomlin, *The Pesticide Manual Incorporating the Agrochemicals Handbook*, 10th Ed., (1995) pp. 193–195.

*Primary Examiner*—Allen J. Robinson
*Attorney, Agent, or Firm*—Birch, Stewart, Kolasch & Birch, LLP

[57] ABSTRACT

There is disclosed a microbicidal composition comprising as active ingredients:

(I) a dithiocarbonimide compound represented by the general formula:

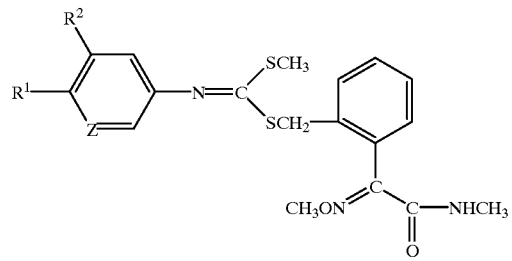

wherein Z represents CH group or nitrogen atom, $R^1$ and $R^2$ are the same or different and represent hydrogen atom, $C_1$–$C_6$ alkyl group, halogen atom, $C_1$–$C_6$ alkoxy group, $C_1$–$C_6$ haloalkyl group or $C_1$–$C_6$ haloalkoxy group, or $R^1$ and $R^2$ are taken together to form methylenedioxy group optionally substituted with fluorine atom, and (II) at least one compound selected from the group consisting of ethylenebis (dithiocarbamate) compound, copper compound, phthalimide microbicidal compound, chlorothalonil, anilide microbicidal compound, cymoxanil, dimethomorph and fosetyl.

7 Claims, No Drawings

MICROBICIDAL COMPOSITION

This application is a divisional of copending application Ser. No. 08/808,552 filed on Feb. 28, 1997, now U.S. Pat. No. 5,798,384, the entire contents of which are hereby incorporated by reference.

FIELD OF THE INVENTION

The present invention relates to a microbicidal composition. More particularly, the present invention relates to a microbicidal composition showing the superior effects of controlling diseases caused by Oomycetes.

BACKGROUND OF THE INVENTION

There have been hitherto known many microbicidal compositions. However, many of diseases caused by Oomycetes have the rapid development of disease symptom once attacked with Oomycetes, and its pathogenic microorganism spreads rapidly by secondary infection. Therefore, the diseases caused by Oomycetes are difficult to effectively control. Thus, there is a great demand for a microbicidal composition showing the superior effects of controlling the diseases caused by Oomycetes.

OBJECTS OF THE INVENTION

A main object of the invention is to provide a microbicidal composition having the superior effects of controlling the diseases caused by Oomycetes.

This object as well as other objects and advantages of the present invention will become apparent to those skilled in the art from the following description.

SUMMARY OF THE INVENTION

The present invention is to solve the above problems and provides a microbicidal composition comprising as active ingredients:

(I) a dithiocarbonimide compound (referred to as "Compound (I)" hereinafter) represented by the general formula:

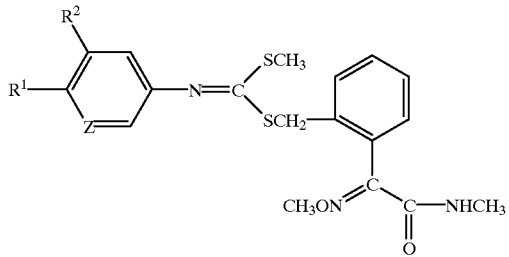

wherein Z represents CH group or nitrogen atom, $R^1$ and $R^2$ are the same or different and represent hydrogen atom, $C_1$–$C_6$ alkyl group, halogen atom, $C_1$–$C_6$ alkoxy group, $C_1$–$C_6$ haloalkyl group or $C_1$–$C_6$ haloalkoxy group, or $R^1$ and $R^2$ are taken together to form methylenedioxy group optionally substituted with fluorine atom, and (II) at least one compound (referred to as "Compound (II)" hereinafter) selected from the group consisting of ethylenebis (dithiocarbamate) compound, copper compound, phthalimide microbicidal compound, chlorothalonil, anilide microbicidal compound, cymoxanil, dimethomorph and fosetyl.

DETAILED DESCRIPTION OF THE INVENTION

At first, Compound (I) is explained.

In the above general formula, examples of $C_1$–$C_6$ alkyl group represented by $R^1$ and $R^2$ are methyl group and ethyl group. Examples of halogen atom are fluorine atom and chlorine atom. Examples of $C_1$–$C_6$ alkoxy group are methoxy group and ethoxy group. An example of $C_1$–$C_6$ haloalkyl group is trifluoromethyl group. An example of $C_1$–$C_6$ haloalkoxy group is trifluoromethoxy group.

Compound (I) can be prepared by a method described in EP-A-0656351.

The embodiments of Compound (I) are shown together with the compound numbers in Table 1 (The embodiments are shown by the definition of respective substituents in the compound represented by the general formula).

| Compound No. | Z | $R^1$ | $R^2$ |
|---|---|---|---|
| (Ia) | CH | $CH_3$ | H |
| (Ib) | CH | $C_2H_5$ | H |
| (Ic) | CH | $OC_2H_5$ | H |
| (Id) | CH | $CF_3$ | H |
| (Ie) | CH | $OC_2H_5$ | F |
| (If) | CH | $OCF_2O$ | |
| (Ig) | N | $OC_2H_5$ | H |
| (Ih) | CH | $CF_3O$ | H |

Then, Compound (II) is explained. Each page described after the name of each compound represents the page where each compounds is described in "The Pesticide Manual, Tenth Edition (edited by Clive Tomlin, published by The British Crop Protection Council and The Royal Society of Chemistry, 1994)".

In the present invention, the ethylenebis-(dithiocarbamate) compound means a salt of ethylenebis-(dithiocarbamate) such as zinc salt [general name; zineb, chemical name; zinc ethylenebis(dithiocarbamate) (polymeric), page 1048], manganese salt [general name; maneb, chemical name; manganese ethylenebis (dithiocarbamate)(polymeric), page 637] and salt of zinc and manganese [general name; manzeb, another name; mancozeb, chemical name; manganese ethylenebis (dithiocarbamate)(polymeric)complex with zinc salt, page 635].

The copper compound means an inorganic salt of copper which is used as a microbicidal agent {such as chloride, oxychloride [general name; basic copper chloride (copper oxychloride), chemical name; dicopper chloride trihydroxide (approximate composition), page 230], carbonate, oxide, hydroxide, sulfate (page 231), phosphate, silicate, zinc chromate and hydrazinium sulfate} and an organic salt of copper which is used as a microbicidal agent {such as acetate, 8-hydroxyquinolinolate [general name; oxine-copper, chemical name; cupric 8-quinolinoxide, page 758], oxalate, bis(3-phenylsalicylate), naphthenate (page 716), linolenate and oleate}.

The phthalimide microbicidal compound means N-(trichloromethylthio)phthalimide {general name; folpet, page 518} which is a compound having the N-substituted phthalimide structure, and N-(trichloromethylthio) cyclohex-4-ene-1,2-dicarboximide (general name; captan, page 145) and N-(1,1,2,2-tetrachloroethylthio)cyclohex-4-ene-1,2-dicarboximide (general name; captafol, page 143) which are a compound having the N-substituted tetrahydrophthalimide structure.

Chlorothalonil (general name) means tetrachloroisophthalonitrile (page 193).

The anilide microbicidal compound means a compound having the 2,6-dimethylanilide structure such as metalaxyl (general name){chemical name; methyl N-(2,6-dimethylphenyl)-N-(methoxyacetyl)alaninate, page 660}, benalaxyl (general name){chemical name; methyl N-(2,6-dimethylphenyl)-N-(phenylacetyl)alaninate, page 71), furalaxyl (general name){chemical name; methyl N-(2,6-dimethylphenyl)-N-(2-furanylcarbonyl)alaninate, page 534}, ofurace (general name){chemical name; 2-chloro-N-(2,6-dimethylphenyl)-N-(tetrahydro-2-oxo-3-furanyl)acetamide, page 745} and oxadixyl (general name){chemical name; 2-methoxy-N-(2-oxo-1,3-oxazolidin-3-yl)aceto-2',6'-xylidide, page 755}, and a compound having the 3-chloroanilide structure such as cyprofuram (general name){chemical name; N-(3-chlorophenyl)-N-(tetrahydro-2-oxo-3-furanyl)cyclopropanecarboxamide, page 1076).

Cymoxanil (general name) means 2-cyano-N-[(ethylamino)carbonyl]-2-(methoximino)acetamide (page 257).

Dimethomorph (general name) means 4-[3-(4-chlorophenyl)-3-(3,4-dimethoxyphenyl)acryloyl]morpholine (page 351).

Fosetyl (general name) means ethyl hydrogen phosphonate (page 530). Fosetyl may be used as a salt such as aluminium salt and the like.

The microbicidal composition of the present invention can be used for controlling disease caused by *Pyricularia oryzae, Cochliobolus miyabeanus* and *Rhizoctonia solani* of rice, *Erysiphe graminis*, f. sp.*hordei*, f. sp.*tritici*, *Gibberella zeae, Puccinia striiformis, P.graminis, P.recondita, P.hordei,* Typhula sp. *Micronectriella nivalis, Ustilago tritici, U. nuda, Tilletia caries, Pseudocercosporella herpotrichoides, Rhizoctonia cerealis, Rhynchosporium secalis, Septoria tritici* and *Leptosphaeria nodorum* of cereal, *Diaporthe citri Elsinoe fawcetti, Penicillium digitatum*, and *P. italicum* of oranges, *Sclerotinia mali, Valsa mali, Podosphaera leucotricha, Alternaria mali* and *Venturia inaequalis* of apple, *Venturia nashicola, Alternaria kikuchiana* and *Gymnosporangium haraeanum* of pear, *Sclerotinia cinerea, Cladosporium carpophilum* and Phomopsis sp. of peach, *Plasmopara viticola, Elsinoe, ampelina, Glomerella cingulata, Uncinula necator* and *Phakopsora ampelopsidis* of vine, *Gloeosporium kaki, Cercospora kaki* and *Mycospharella nawae* of persimmon, *Pseudoperonospora cubensis* of cucumber, *Colletotrichum lagenarium, Sphaerotheca fuliginea, Mycosphaerella melonis* of Cucurbitaceae plants, *Alternaria solani, Cladosporium fulvum* and *Phytophthora infestans* of tomato, *Phomopsis vexans* and *Erysiphe cichoracearum* of egg plant, *Alternaria japonica* and *Cercosporella brassicae* of Cruciferae plants, *Puccinia allii* of Welsh onion, *Cercospora kikuchii, Elsinoe glycines* and *Diaporthe phaseolorum* var. *saiae* of soybean, *Colletotrichum lindemthianum* of kidney bean, *Mycosphaerella personatum* and *Cercospora arachidicola* of peanut, *Erysiphe pisi* and *Peronospora pisi* of garden pea, *Peronospora viciae* and *Phytophthora nicotianae* of broad bean, *Alternaria solani* and *Phytophthora infestans* of potato, *Sphaetotheca humuli* and *Phytophthora nicotianae* of strawberry, *Exobasidium reticulatum* and *Elsinoe leucospila* of tea, *Alternaria longipes, Erysiphe cichoracearum, Colletotrichum tabacum* and *Phytophthora parasitica* of tobacco, *Cercospora beticola, Diplocarpon rosae, Sphaerotheca pannosa* and *Phytophthora megasperma* of rose, *Septoria chrysanthemi-indici* and *Puccinia horiana* of chrysanthemum, *Botrytis cinerea* and *Sclerotinia sclerotiorum* of various crops, and various diseases caused by Pythium sp. In particular, the microbicidal composition of the present invention shows the superior effects by its synergistic microbicidal effects in controlling Oomycetes diseases caused by such as Peronospora, Phytophthora and Pythium sp.

In the microbicidal composition of the present invention, a mixing ratio of Compound (I) and Compound (II) is not limited to specified ones. An amount of at least one compound selected from the group consisting of ethylenebis (dithiocarbamate) compound, copper compound, phthalimide microbicidal compound, chlorothalonil and fosetyl is usually in a range of 0.1 to 100 parts by weight, preferably 0.5 to 50 parts by weight based on 1 part by weight of Compound (I). An amount of the anilide microbicidal compound is usually in a range of 0.01 to 20 parts by weight, preferably 0.1 to 10 parts by weight based on 1 part by weight of Compound (I). An amount of cymoxanil is usually in a range of 0.1 to 100 parts by weight, preferably 0.5 to 50 parts by weight based on 1 part by weight of Compound (I). An amount of dimethomorph is usually in a range of 0.1 to 50 parts by weight, preferably 0.2 to 10 parts by weight based on 1 part by weight of Compound (I).

The microbicidal composition of the present invention can be used merely by mixing Compound (I) and Compound (II). However, the microbicidal composition of the present invention is usually used by formulating into preparations such as water dispersible powder, suspension, granule, dry-flowable agent, emulsifiable concentrate, liquid formulation, oil solution, smoking agent, aerosol agent and microcapsule, by mixing Compound (I) and Compound (II), mixing the mixture with solid carrier, liquid carrier and/or gaseous carrier and, if necessary, adding thereto an adjuvant for preparations such as surfactant, adhesive agent, dispersing agent and stabilizing agent. Alternatively, the microbicidal composition of the present invention may be used by formulating Compound (I) and Compound (II) into preparations separately, diluting each preparation with water and mixing both preparations. A total amount of active ingredient compounds contained in these preparations is usually 0.1 to 99% by weight, preferably 0.2 to 90% by weight.

Examples of the solid carrier are pulverized or particulate clay (such as kaolin clay, diatomaceous earth, synthetic hydrated silicon oxide, attapulgite clay, bentonite and acid clay), talcs, other inorganic minerals (such as sericite, quartz powder, sulfur powder, activated carbon, calcium carbonate and hydrated silica), and salt for chemical fertilizer (such as ammonium sulfate, ammonium phosphate, ammonium nitrate, urea and ammonium chloride). Examples of the liquid carrier are water, alcohols (such as methanol and ethanol), ketones (such as acetone, methyl ethyl ketone and cyclohexanone), aromatic hydrocarbons (such as benzene, toluene, xylene, ethylbenzene and methylnaphthalene), aliphatic hydrocarbons (such as hexane and kerosene), esters (such as ethyl acetate and butyl acetate), nitrites (such as acetonitrile and isobutyronitrile), ethers (such as dioxane and diisopropyl ether), acid amides (such as dimethylformamide and dimethylacetamide), halogenated hydrocarbons (such as dichloroethane, trichloroethylene and carbon tetrachloride). Examples of the gaseous carrier are butane gas, carbonic acid gas and fluorocarbon gas.

Examples of the surfactant are alkylsulfuric esters, alkylsulfonate, alkylarylsulfonate, alkyl aryl ether and its polyoxyethylene compound, polyethylene glycol ether, multivalent alcohol ester and sugar alcohol derivative.

Examples of the adhesive agent and the dispersing agent are casein, gelatin, polysaccharides (such as starch, acacia, cellulose derivative and alginic acid), lignin derivative, bentonite, sugars, and synthetic water-soluble polymer (polyvinyl alcohol, polyvinyl pyrrolidone and polyacrylic acid). Examples of the stabilizing agent are PAP (acid isopropyl phosphate), BHT (2,6-di-tert-butyl-4-methylphenol), BHA (mixture of 2-tert-butyl-4-methoxyphenol and 3-tert-butyl-4-methoxyphenol), vegetable oil, mineral oil, and fatty acid or ester thereof.

The above-described preparations are applied to plants or soil as they are or by diluting with water or the like. When the preparations are applied to soil, they may be sprayed to the surface of soil or may be used by applying in admixture with the soil. Alternatively, the preparations may be applied by various methods such as seed treatment method and ULV method. When the preparations are used as a seed treating agent, they are used by seed coating treatment, seed soaking treatment, seed spraying treatment or the like.

The microbicidal composition of the present invention may be used together with other microbicidal agent, insecticide, acaricide, nematicide, herbicide, seed disinfectant, fertilizer, soil conditioner and the like.

An amount of application of the microbicidal composition of the present invention depends upon kind of active ingredient compound, mixing ratio of Compound (I) and Compound (II), weather conditions, preparation form, application time, application method, application place, subject disease damage, subject crop and the like and a total amount of the active ingredient compounds is usually is 0.001 to 1000 g/are, preferably 0.1 to 100 g/are. When emulsifiable concentrate, water dispersible powder, suspension, liquid formulation or the like is applied, the application concentration is usually 0.0001 to 1% by weight, preferably 0.001 to 0.5% by weight. Granule, powder or the like is applied as it is without dilution. Upon seed treatment, the total amount of active ingredient compounds to be applied is usually 0.001 to 50 g/kg seed, preferably 0.01 to 10 g/kg seed.

The following Preparation Examples and Test Examples illustrate the present invention in detail but are not to be construed to limit the scope thereof.

"Part" means "part by weight" unless otherwise indicated.

PREPARATION EXAMPLE 1

One part of Compound (Ia), (Ib), (Ic), (Id), (Ie), (If), (Ig) or (Ih); 5 parts of zineb, maneb, manzeb, inorganic salt of copper, organic salt of copper, folpet, captan, captafol, chlorothalonil, metalaxyl, benalaxyl, furalaxyl, ofurace, oxadixyl, cyprofuram, cymoxanil, dimethomorph or fosetyl; one part of synthetic hydrated silicon oxide; 2 parts of calcium lignin sulfonate; 30 parts of bentonite and 61 parts of kaolin clay are well ground and mixed, water is added thereto to well knead together, followed by granulation and drying to obtain granules.

PREPARATION EXAMPLE 2

5 Parts of Compound (Ia), (Ib), (Ic), (Id), (Ie), (If), (Ig) or (Ih); 5 parts of zineb, maneb, manzeb, inorganic salt of copper, organic salt of copper, folpet, captan, captafol, chlorothalonil, metalaxyl, benalaxyl, furalaxyl, ofurace, oxadixyl, cyprofuram, cymoxanil, dimethomorph or fosetyl; one part of synthetic hydrated silicon oxide; 2 parts of calcium lignin sulfonate; 30 parts of bentonite and 57 parts of kaolin clay are well ground and mixed, water is added thereto to well knead together, followed by granulation and drying to obtain granules.

PREPARATION EXAMPLE 3

0.5 Part of Compound (Ia), (Ib), (Ic), (Id), (Ie), (If), (Ig) or (Ih); 2.5 parts of zineb, maneb, manzeb, inorganic salt of copper, organic salt of copper, folpet, captan, captafol, chlorothalonil, metalaxyl, benalaxyl, furalaxyl, ofurace, oxadixyl, cyprofuram, cymoxanil, dimethomorph or fosetyl; 86 parts of kaolin clay and 11 parts of talc are well ground and mixed to obtain powders.

PREPARATION EXAMPLE 4

5 Parts of Compound (Ia), (Ib), (Ic), (Id), (Ie), (If), (Ig) or (Ih); 25 parts of zineb, maneb, manzeb, inorganic salt of copper, organic salt of copper, folpet, captan, captafol, chlorothalonil, metalaxyl, benalaxyl, furalaxyl, ofurace, oxadixyl, cyprofuram, cymoxanil, dimethomorph or fosetyl; 3 parts of polyoxyethylene sorbitan monooleate; 3 parts of carboxymethyl cellulose and 64 parts of water are mixed and wet-ground to the particle size of less than 5 microns to obtain suspensions.

PREPARATION EXAMPLE 5

10 Parts of Compound (Ia), (Ib), (Ic), (Id), (Ie), (If), (Ig) or (Ih); 50 parts of zineb, maneb, manzeb, inorganic salt of copper, organic salt of copper, folpet, captan, captafol, chlorothalonil, metalaxyl, benalaxyl, furalaxyl, ofurace, oxadixyl, cyprofuram, cymoxanil, dimethomorph or fosetyl; 3 parts of calcium lignin sulfonate; 2 parts of sodium lauryl sulfate and 35 parts of synthetic hydrated silicon oxide are well ground and mixed to obtain water dispersible powders.

The following Test Examples indicate that the microbicidal composition of the present invention has the excellent disease controlling activity.

Controlling effect, which is expected when treatment is carried out by mixing the given two kinds of active ingredient compounds, is generally calculated according to the following Colby equation.

$$E = X + Y - \frac{X \times Y}{100}$$

X: Controlling value (%) when treatment is carried out by using an active ingredient compound A at the concentration of m ppm Y: Controlling value (%) when treatment is carried out by using an active ingredient compound B at the concentration of n ppm E: Controlling value (%) when treatment is carried out by using the active ingredient compound A at the concentration of m ppm and the active ingredient compound B at the concentration of n ppm (hereinafter referred to as "expected controlling value").

If controlling value (%) when treatment is carried out by actually mixing two kinds of active ingredient compounds is greater than the expected controlling value (%), it can be said that there is the synergistic effect in a combination of those compounds.

TEST EXAMPLE 1

Sandy loam was filled into a plastic pot, a vine (Berry A) was seeded thereto, the vine was grown for 40 days in a greenhouse. A test preparation, which had formulated into water dispersible powder according to Preparation Example 5, was diluted with water to a predetermined concentration. The diluted test preparation was sprayed to foliage of a vine seedling having developed three true leaves so as to effectively attach to the leaf surface. Then, the seedling was spray-inoculated with a zoosporangium suspension of *Plas-* mopara viticola. After inoculation, the seedling was placed under high humidity at 23° C. overnight, grown for 7 days in a greenhouse, severity (%) was investigated and the actual controlling value (%) was obtained according to the following equation.

Controlling value (%)={[Severity of non-treated plant (%)–severity of treated plant (%)]/[severity of non-treated plant (%)]}× 100

The results are shown in Table 2

TABLE 2

| Test compound | Concentration of active ingredient (ppm) | Actual controlling value (%) | Expected controlling value (%) |
|---|---|---|---|
| (Ia) + manzeb | 0.8 + 11 | 90 | 63 |
| (Ib) + manzeb | 0.8 + 11 | 94 | 74 |
| (Ic) + manzeb | 0.8 + 11 | 90 | 66 |
| (Ia) + copper oxychloride | 0.8 + 11 | 83 | 60 |
| (Ic) + copper oxychloride | 0.8 + 11 | 80 | 64 |
| (Ig) + copper oxychloride | 0.8 + 11 | 90 | 72 |
| (Ia) + folpet | 0.8 + 8 | 90 | 55 |
| (Ib) + folpet | 0.8 + 8 | 92 | 67 |
| (Id) + folpet | 0.8 + 8 | 88 | 60 |
| (Ia) + chlorothalonil | 0.8 + 10 | 70 | 53 |
| (Ic) + chlorothalonil | 0.8 + 10 | 70 | 57 |
| (Ig) + chlorothalonil | 0.8 + 10 | 80 | 67 |
| (Ia) + metalaxyl | 0.8 + 0.5 | 90 | 68 |
| (Ib) + metalaxyl | 0.8 + 0.5 | 95 | 76 |
| (Ig) + metalaxyl | 0.8 + 0.5 | 95 | 77 |
| (Ib) + cymoxanil | 0.8 + 30 | 82 | 67 |
| (Ic) + cymoxanil | 0.8 + 30 | 76 | 60 |
| (Id) + cymoxanil | 0.8 + 30 | 70 | 51 |
| (Ia) + dimethomorph | 0.8 + 1 | 85 | 60 |
| (Ic) + dimethomorph | 0.8 + 1 | 85 | 64 |
| (Ig) + dimethomorph | 0.8 + 1 | 90 | 72 |
| (Ia) + fosetyl | 0.8 + 8 | 90 | 50 |
| (Ib) + fosetyl | 0.8 + 8 | 95 | 63 |
| (Id) + fosetyl | 0.8 + 8 | 90 | 45 |
| (Ia) | 0.8 | 50 | — |
| (Ib) | 0.8 | 63 | — |
| (Ic) | 0.8 | 55 | — |
| (Id) | 0.8 | 45 | — |
| (Ig) | 0.8 | 65 | — |
| Manzeb | 11 | 25 | — |
| Copper oxychloride | 11 | 20 | — |
| Folpet | 8 | 10 | — |
| Chlorothalonil | 10 | 5 | — |
| Metalaxyl | 0.5 | 35 | — |
| Cymoxanil | 30 | 10 | — |
| Dimethomorph | 1 | 20 | — |
| Fosetyl | 8 | 0 | — |

TEST EXAMPLE 2

Sandy loam was filled into a plastic pot, a tomato (Ponterosa) was seeded thereto, the tomato was grown for 20 days in a greenhouse. A test preparation, which had formulated into suspension according to Preparation Example 4, was diluted with water to a predetermined concentration. The diluted test preparation was sprayed to foliage of a tomato seedling having developed two true leaves so as to effectively attach to the leaf surface. Then, the seedling was spray-inoculated with a zoosporangium suspension of *Phytophthora infestans*. After inoculation, the seedling was placed under high humidity at 23° C. overnight, grown for 4 days in a greenhouse, severity (%) was investigated and the actual controlling value (%) was obtained according to the above equation.

The results are shown in Table 3

TABLE 3

| Test Compound | Concentration of active ingredient (ppm) | Actual controlling value (%) | Expected controlling value (%) |
|---|---|---|---|
| (Ia) + manzeb | 12.5 + 12.5 | 100 | 90 |
| (Ib) + manzeb | 12.5 + 12.5 | 100 | 95 |
| (Id) + manzeb | 12.5 + 12.5 | 100 | 85 |
| (Ib) + chlorothalonil | 12.5 + 12.5 | 100 | 95 |
| (Ic) + chlorothalonil | 12.5 + 12.5 | 100 | 96 |
| (Id) + chlorothalonil | 12.5 + 12.5 | 100 | 85 |
| (Ia) + metalaxyl | 12.5 + 12.5 | 100 | 85 |
| (Ib) + metalaxyl | 12.5 + 12.5 | 100 | 93 |
| (Ic) + metalaxyl | 12.5 + 12.5 | 100 | 94 |
| (Id) + metalaxyl | 12.5 + 12.5 | 100 | 78 |
| (Ie) + metalaxyl | 12.5 + 12.5 | 100 | 94 |
| (If) + metalaxyl | 12.5 + 12.5 | 100 | 90 |
| (Ig) + metalaxyl | 12.5 + 12.5 | 100 | 94 |
| (Ih) + metalaxyl | 12.5 + 12.5 | 100 | 93 |
| (Ib) + cymoxanil | 12.5 + 50 | 100 | 93 |
| (Ic) + cymoxanil | 12.5 + 50 | 100 | 95 |
| (Ig) + cymoxanil | 12.5 + 50 | 100 | 95 |
| (Ia) + dimethomorph | 12.5 + 12.5 | 100 | 92 |
| (Ic) + dimethomorph | 12.5 + 12.5 | 100 | 95 |
| (Ig) + dimethomorph | 12.5 + 12.5 | 100 | 95 |
| (Ia) | 12.5 | 80 | — |
| (Ib) | 12.5 | 90 | — |
| (Ic) | 12.5 | 92 | — |
| (Id) | 12.5 | 70 | — |
| (Ie) | 12.5 | 92 | — |
| (If) | 12.5 | 86 | — |
| (Ig) | 12.5 | 92 | — |
| (Ih) | 12.5 | 90 | — |
| Manzeb | 12.5 | 50 | — |
| Chlorothalonil | 12.5 | 50 | — |
| Metalaxyl | 5 | 25 | — |
| Cymoxanil | 50 | 33 | — |
| Dimethomorph | 12.5 | 60 | — |

The following Preparation Example illustrates the preparation of Compound (I) used in the present invention Reference Preparation Example [Preparation of Compound (Ie)]

Carbon disulfide (2.0 g, 26 mmol) was added to a mixture of 4-ethoxy-3-fluoroaniline (2.7 g, 17 mmol) and triethylamine (4.0 g, 40 mmol) while stirring. The mixture was stirred at room temperature for 10 hours, N,N-dimethylformamide (30 ml) was added thereto and methyl iodide (2.2 g, 16 mmol) was added dropwise. The mixture was stirred at room temperature for 30 minutes and dilute hydrochloric acid was added thereto, followed by extraction with diethyl ether. The organic layer was washed with a saturated sodium chloride solution, dried with anhydrous sodium sulfate and concentrated under reduced pressure. The residue was subjected to silica gel column chromatography (elution solvent; hexane:ethyl acetate=4:1) to obtain methyl 4-ethoxy-3-fluorophenyldithiocarbamate (2.5 g, 10 mmol) as crystals. m.p. 108.0° C.

Sodium hydride (60% oil dispersion, 60 mg, 1.5 mmol). was added to a solution of 4-ethoxy-3-fluorophenyldithiocarbamate (0.40 g, 1.6 mmol) in tetrahydrofuran (20 ml) at room temperature. The mixture was stirred at room temperature for 30 minutes and (E)-methoximino-2-(2-bromomethylphenyl)-N-methylacetamide (0.42 g, 1.5 mmol) was added thereto. The mixture was stirred at room temperature for 30 minutes and water was added thereto, followed by extraction with ethyl acetate. The organic layer was dried with anhydrous magnesium sulfate and concentrated under reduced pressure. The residue was subjected to silica gel column chromatography (elution solvent; hexane:ethyl acetate=1:1) to obtain (E)-2-methoximino-2-[2-(4-ethoxy-3-fluorophenylimino) (methylthio)methylthiophenyl]-N-methylacetamide (0.60 g, 1.3 mmol) as an oil.

$^1$H-NMR (CDCl$_3$/TMS, δ (ppm)) 1.26 (3H, t, J=7.1 Hz), 2.45 (3H, s), 2.88 (3H, d, J=4.6 Hz), 2.95 (3H, s), 4.12 (2H, q, J=7.1 Hz), 4.22 (2H, br s), 6.55–7.50 (8H, m).

Some NMR data of the other compounds used in the present invention are shown below.

Compound (Ia):

$^1$H-NMR (CDCl$_3$/TMS, δ (ppm)) 2.46 (3H, s), 2.89 (3H, d, J=5.0 Hz), 3.95 (3H, s), 4.21 (2H, br s), 6.51–7.46 (8H, m).

Compound (If):

$^1$H-NMR (CDCl$_3$/TMS, δ (ppm)) 2.31 (3H,s), 2.44 (3H, s), 2.86 (3H, d, J=5.0 Hz), 3.95 (3H, s), 4.22 (2H, br s), 6.72–7.49 (9H, m).

What is claimed is:

1. A microbicidal composition comprising synergistic microbicidally effective amounts of the mixture of active ingredients:

(I) a dithiocarbonimide compound represented by the formula:

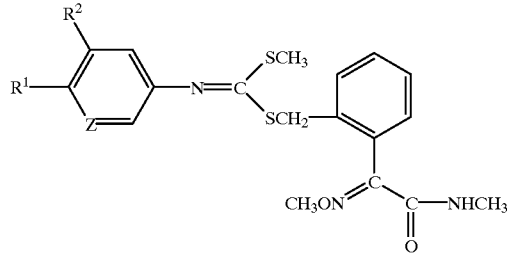

wherein

Z represents CH group, $R^1$ and $R^2$ are the same or different and represent hydrogen atom, $C_1$–$C_6$ alkyl group, halogen atom, $C_1$–$C_6$ alkoxy group, $C_1$–$C_6$ haloalkyl group or $C_1$–$C_6$ haloalkoxy group and (II) fosetyl or a salt thereof, wherein a weight ratio of compound (I) to compound (II) is 1:0.1 to 100.

2. The microbicidal composition according to claim 1, wherein the weight ratio of compound (I) to compound (II) is 1:0.5 to 50.

3. A microbicidal composition comprising synergistic microbicidally effective amounts of the mixture of active ingredients:

(I) a dithiocarbonimide compound represented by the formula:

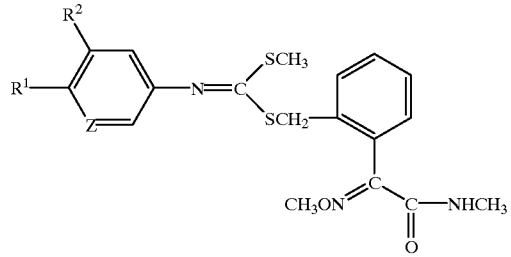

wherein Z represents CH group, $R^1$ is $C_2H_5$, and $R^2$ is hydrogen; and (II) fosetyl or a salt thereof, wherein a weight ratio of compound (I) to compound (II) is 1:0.1 to 100.

4. A method of controlling a disease caused by Oomycetes fungi, which comprises applying a synergistic fungicidally effective amount of the composition as defined in claim 1 to a locus where Oomycetes fungi propagate, wherein a total amount of compound (I) and compound (II) is 0.001 to 1000 g/are.

5. The method according to claim 4, wherein the total amount of the compound (I) and compound (II) is 0.1 to 100 g/are.

6. A method of controlling a disease caused by Oomycetes fungi, comprising treating seed with a synergistic fungicidally effective amount of the composition of claim 1 in an amount of 0.001 to 50 g/kg seed as the total amount of compound (I) and compound (II).

7. The method according to claim 6, wherein the total amount of compound (I) and compound (II) is 0.01 to 10 g/kg seed.

* * * * *